US00PP25113P2

(12) United States Plant Patent
Stemkens

(10) Patent No.: US PP25,113 P2
(45) Date of Patent: Nov. 25, 2014

(54) ***IBERIS* PLANT NAMED 'IBSZ0001'**

(50) Latin Name: *Iberis sempervirens*
Varietal Denomination: IBSZ0001

(75) Inventor: Henricus Godefridus Wilhelmus Stemkens, Enkhuizen (NL)

(73) Assignee: Syngenta Crop Protection AG, Basel (CH)

( * ) Notice: Subject to any disclaimer, the term of this patent is extended or adjusted under 35 U.S.C. 154(b) by 242 days.

(21) Appl. No.: 13/507,176

(22) Filed: Jun. 11, 2012

(51) Int. Cl.
*A01H 5/00* (2006.01)

(52) U.S. Cl.
USPC ..... Plt./263.1

(58) Field of Classification Search
CPC ..... A01H 5/02
USPC ..... Plt./263.1
See application file for complete search history.

*Primary Examiner* — Susan McCormick Ewoldt
*Assistant Examiner* — Louanne Krawczewicz Myer
(74) *Attorney, Agent, or Firm* — Joshua L. Price

(57) ABSTRACT

A new *Iberis* plant named 'IBSZ0001' particularly distinguished by the has large white inflorescences that are early flowering, a tightly branched and free flowering habit, with dark glossy leaves.

1 Drawing Sheet

Latin name of the genus and species of the plant claimed: *Iberis sempervirens.*

Varietal denomination: 'IBSZ0001'.

BACKGROUND OF THE NEW PLANT

The present invention comprises a new *Iberis*, botanically known as *Iberis sempervirens*, and hereinafter referred to by the variety name 'IBSZ0001'.

'IBSZ0001' is a product of a planned breeding program. The new cultivar 'IBSZ0001' has large white inflorescences that are early flowering, a tightly branched and free flowering habit, with dark glossy leaves.

'IBSZ0001' originates from a hybridization in a greenhouse in April 2007 in Enkhuizen, The Netherlands. The female parent was an unpatented, proprietary plant designated 'K1007-1' with smaller white flowers, lighter green foliage and is less branched when compared to 'IBSZ0001'.

The male parent of 'IBSZ0001' was an unpatented, proprietary plant identified as 'K1077-1' with larger white flowers, and larger darker green leaves when compared to 'IBSZ0001'. The resultant seed was sown in August 2007 in Enkhuizen, The Netherlands.

'IBSZ0001' was selected as one flowering plant within the progeny of the stated cross in March 2008 in a greenhouse in Enkhuizen, The Netherlands.

The first act of asexual reproduction of 'IBSZ0001' was accomplished when vegetative cuttings were propagated from the initial selection in March 2008 in a greenhouse in Enkhuizen, The Netherlands.

BRIEF SUMMARY OF INVENTION

Horticultural examination of plants grown from cuttings of the plant initiated in March 2008 in Enkhuizen, The Netherlands, and continuing thereafter, has demonstrated that the combination of characteristics as herein disclosed for 'IBSZ0001' are firmly fixed and are retained through successive generations of asexual reproduction.

'IBSZ0001' has not been observed under all possible environmental conditions. The phenotype may vary significantly with variations in environment such as temperature, light intensity and day length.

A Plant Breeder's Right for this cultivar was applied for in Canada on Jun. 7, 2012, No. 12-7627. 'IBSZ0001' has not been made publicly available more than one year prior to the filing of this application.

The following traits have been repeatedly observed and are determined to be basic characteristics of the new variety. The combination of these characteristics distinguishes this Iberis as a new and distinct variety.

BRIEF DESCRIPTION OF THE PHOTOGRAPHS

The accompanying photographic drawings show typical flower and foliage characteristics of 'IBSZ0001' with colors being as true as possible with an illustration of this type.

Figure 1:
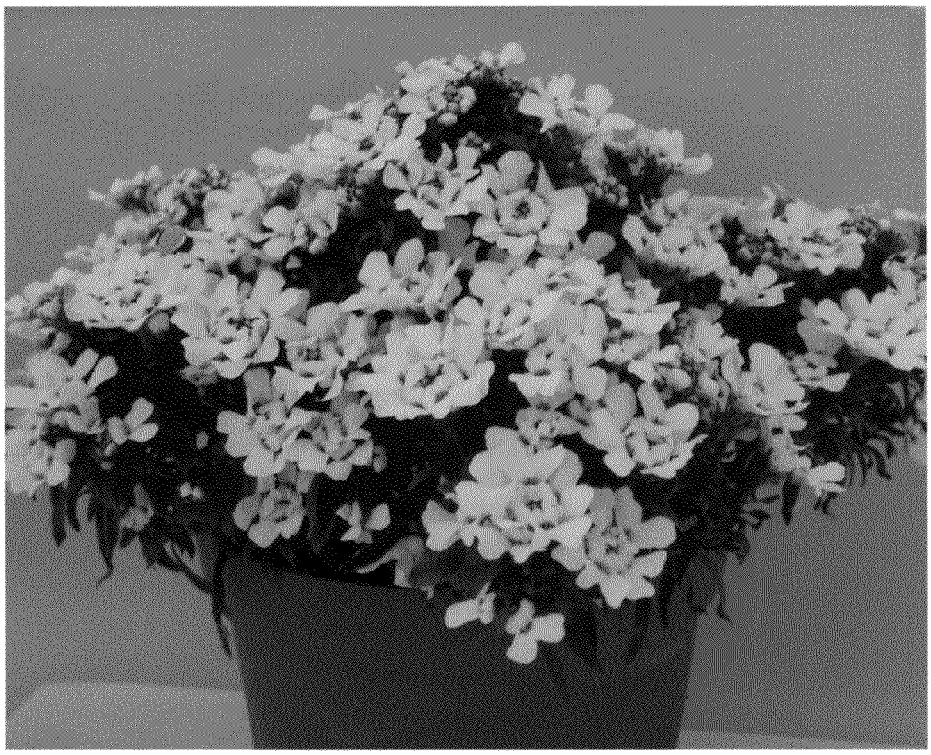
Figure 2:
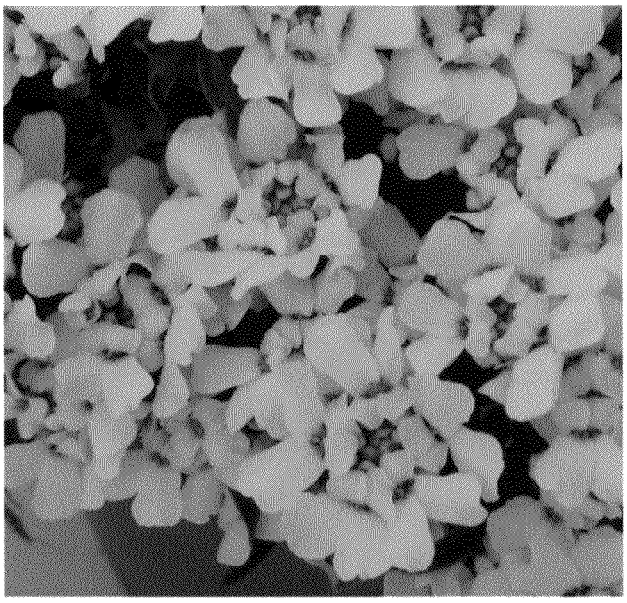

The photographic drawings show in FIG. 1 a flowering plant of the new variety and in FIG. 2 a close-up of the inflorescences.

DETAILED BOTANICAL DESCRIPTION

The plant descriptions and measurements were taken in Gilroy, Calif. under natural light in March 2012. These plants were approximately 25 weeks old and were growing in 1 gallon pots in shade-house trials. The plants used for the photographs were about 28 weeks old growing in Enkhuizen, The Netherlands and the photographs were taken in March 2012.

Color Chart used: Royal Horticultural Society Colour Chart (R.H.S.) 2001

TABLE 1

DIFFERENCES BETWEEN THE NEW VARIETY 'IBSZ0001' AND A SIMILAR VARIETY

| | 'IBSZ0001' | 'Snow Cone' (Unpatented) |
|---|---|---|
| Flower size: | Smaller | Larger |
| Leaf color: | Lighter | Darker |
| Branching habit: | More branching | Less branching |

Plant:

*Form, growth and habit.*—Compact, tightly mounded and branched, freely flowering.

*Plant height.*—10.0-12.0 cm.

*Plant height (inflorescence included).*—15.0-18.0 cm.

*Plant width.*—26.0-30.0 cm.

Roots:

*Number of days to initiate roots.*—About 9 days at about 18 degrees C.

*Number of days to produce a rooted cutting.*—3 weeks at 18 degrees C.

*Type.*—Fine, fibrous, free branching.

*Color.*—RHS N155B but whiter.

Foliage:

*Arrangement.*—Alternate, sessile.

*Immature, leaf color, upper surface.*—RHS 147A.

*Lower surface.*—RHS 137B.

*Mature, leaf color, upper surface.*—RHS 147A.

*Lower surface.*—RHS 137B.

*Length.*—2.0-2.7 cm.

*Width.*—0.5-0.6 cm.

*Shape.*—Linear.

*Base shape.*—Acuminate.

*Apex shape.*—Acute.

*Margin.*—Entire.

*Texture, upper surface.*—Glabrous.

*Lower surface.*—Glabrous.

*Color of veins, upper surface.*—RHS 138B.

*Color of veins, lower surface.*—RHS 138B.

*Venation pattern.*—Pinnate.

Stem:

*Quantity of main branches.*—About 20.

*Color of stem.*—Between RHS 144A and RHS 144B.

*Length of stem.*—12.0-16.0 cm (including peduncle).

*Diameter.*—0.25 cm.

*Length of internodes.*—0.5 cm.

*Texture.*—Pubescent.

Inflorescence:

*Type.*—Short simple corymb.

*Quantity of inflorescences per plant.*—About 80.

*Natural flowering season.*—February to May.

*Inflorescence length.*—About 5.0 cm.

*Inflorescence width.*—3.0-3.4 cm at widest point.

*Lastingness of individual blooms on the plant.*—About 14 days.

*Fragrance.*—None.

Bud (just before opening/showing color):

*Color.*—Closest to RHS N155B but pure white.

*Length.*—0.3 cm.

*Width.*—0.3 cm.

*Shape.*—Globose.

*Pedicel color.*—RHS 144A.

*Pedicel length.*—0.7-0.9 cm.

*Pedicel diameter.*—0.5 cm.

*Pedicel texture.*—Pubescent.

Corolla:

*Floret type.*—4 petals — 2 smaller upper and 2 larger lower; which do not reflex much.

*Floret diameter.*—0.9-1.2 cm at widest part.

*Floret depth.*—0.5 cm.

*Petal (all) color, upper surface.*—Closest to RHS N155B but pure white.

*Lower surface.*—Closest to RHS N155B but pure white.

*Upper/shorter petals.*—

*Length.*—0.25 cm.

*Width.*—0.3 cm.

*Shape.*—Oblate.

*Apex shape.*—Rounded.

*Margin.*—Entire.

*Lower/longer petals.*—

*Length.*—1.0-1.1 cm.

*Width.*—0.5-0.6 cm.

*Shape.*—Oblong.

*Apex shape.*—Rounded.

*Margin.*—Entire but some very slightly retuse.

*Petal (all) texture, upper surface.*—Papillose.

*Lower surface.*—Papillose.

Calyx:

*Quantity.*—4 sepals, arranged in a whorl.

*Height of calyx.*—About 3 mm.

*Diameter of calyx.*—4 mm.

*Color, upper surface.*—RHS 144B with RHS 155D margins.

*Lower surface.*—RHS 144B with RHS 155D margins.

*Length of sepal.*—0.25-0.3 cm.

*Width of sepal.*—0.15-0.2 cm.

*Shape of sepal.*—Ovate.

*Apex shape.*—Obtuse

*Base.*—Fused

*Margins.*—Entire

*Texture, upper/inner surface.*—Glabrous

*Lower/outer surface.*—Glabrous

Reproductive organs:

*Gynoecium.*—

*Pistil quantity.*—1.

*Length.*—0.22 cm.

*Style color.*—RHS 145B.

*Style length.*—0.1 cm.

*Stigma color.*—RHS 145A.

*Stigma shape.*—Bi-lobed.

*Ovary.*—Not very discernable.

*Androecium stamens, quantity.*—6; 4 longer, 2 shorter.

*Color of filaments.*—Lighter than RHS N144A.

*Length of longer filaments.*—0.2 cm.

*Length of shorter filaments.*—0.1.

*Anther color.*—RHS 6B.

*Anther length.*—0.05 cm.

*Anther shape.*—Oval.

*Color of pollen.*—RHS 13B.

*Pollen amount.*—Normal.

*Fertility/seed set.*—Has not determined to date.

*Disease/pest resistance.*—Has not been determined to date.

What is claimed is:

1. A new and distinct variety of *Iberis* plant named 'IBSZ0001' substantially as illustrated and described herein.

* * * * *